(12) United States Patent
Chien et al.

(10) Patent No.: US 6,391,540 B1
(45) Date of Patent: May 21, 2002

(54) METHOD FOR DETECTING ANTIBODIES IN A SAMPLE

(75) Inventors: David Y. Chien; Phillip Arcangel; Stephen Tirell; Wanda Zeigler, all of Emeryville, CA (US)

(73) Assignee: Chiron Corporation, Emeryville, CA (US)

( * ) Notice: Subject to any disclaimer, the term of this patent is extended or adjusted under 35 U.S.C. 154(b) by 0 days.

(21) Appl. No.: 09/158,301

(22) Filed: Sep. 22, 1998

Related U.S. Application Data

(60) Provisional application No. 60/059,703, filed on Sep. 22, 1997, and provisional application No. 60/083,921, filed on May 1, 1998.

(51) Int. Cl.$^7$ .............................................. C12Q 1/70
(52) U.S. Cl. .................... 435/5; 435/7.94; 435/7.95; 436/518; 436/820
(58) Field of Search ................... 435/5, 7.94, 7.95; 436/518, 820

(56) References Cited

U.S. PATENT DOCUMENTS

| | | | |
|---|---|---|---|
| 4,737,453 A | 4/1988 | Primus | 435/5 |
| 5,395,752 A | 3/1995 | Law et al. | 435/6 |
| 5,616,460 A | 4/1997 | Figard | 435/5 |
| 5,681,695 A | 10/1997 | Decker et al. | 435/5 |
| 5,705,330 A | 1/1998 | Shah et al. | 435/5 |
| 5,773,212 A | 6/1998 | Figard | 435/5 |

FOREIGN PATENT DOCUMENTS

| | | |
|---|---|---|
| DE | 195 02 386 A1 | 8/1996 |
| EP | 0 341 439 A | 11/1989 |
| FR | 2 556 840 | 6/1985 |
| WO | WO 92/08979 | 5/1992 |
| WO | WO 93/14403 | 7/1993 |
| WO | WO 94/24560 | 10/1994 |
| WO | WO 94/25874 | 11/1994 |
| WO | WO 94/26932 | 11/1994 |
| WO | WO 95/27702 | 10/1995 |
| WO | WO 97/44469 | 11/1997 |

OTHER PUBLICATIONS

Cohard, M. et al., "Hepatitis C virus–specific CTL responses in PBMC from chimpanzees with chronic hepatitis C: determination of CTL and CTL precursor frequencies using a recombinant canarypox virus (ALVAC)", *J. Immunol. Methods*, 1998, 214(1–2), 121–129.

Ide, Y. et al., "Hepatitis C virus NS5A protein is phosphorylated in vitro by a stably bound protein kinase from HeLa cells and by cAMP–dependent protein kinase A–alpha catalytic subunit", *Gene*, 1997, 201(1–2), 151–158.

Patent Abstracts of Japan, JP 06–074956 A, published Mar. 18, 1994, 1 page.

Chien et al., "Diagnosis of hepatitis C virus (HCV) infection using an immunodominant chimeric polyprotein to capture circulating antibodies: Reevaluation of the role of HCV in liver disease," *Proc. Natl. Acad. Sci. USA*, 1992, 89, 10011–10015.

Choo et al., "Isolation of a cDNA Clone Derived from a Blood–Borne Non–A, Non–B Viral Hepatitis Genome," *Science*, 1989, 244, 359–362.

Cousens et al., "High level expression of proinsulin in the yeast, *Saccharomyces cerevisiae* ," *Gene*, 1987, 61, 265–275.

Kuo et al., "An Assay for Circulating Antibodies to a Major Etiologic Virus of Human Non–A, Non–B Hepatitis," *Science*, 1989, 244, 362–364.

*Primary Examiner*—Donna C. Wortman
(74) *Attorney, Agent, or Firm*—Paul K. Legaard; Alissa A. Harbin; Robert B. Blackburn

(57) ABSTRACT

The present invention is directed to assays for detecting antibodies in a sample in a single incubation step. The assays employ universal solid phases and/or universal detectable markers, and facilitate the detection and differentiation of antigens from the same source or from different sources in a single test sample. The present invention includes test kits for performing the methods according to the invention.

33 Claims, 1 Drawing Sheet

METHOD FOR DETECTING ANTIBODIES IN A SAMPLE

This application claims priority benefit under 35 U.S.C. §119 to application Ser. Nos. 60/059,703 filed Sep. 22, 1997 and 60/083,921, filed May 1, 1998 hereby incorporated by reference in their entireties.

FIELD OF THE INVENTION

The present invention relates to the detection/quantitation of antibodies against antigens in a sample.

BACKGROUND OF THE INVENTION

Antibody capture assays are generally used for the detection of antibodies directed to particular antigens in a sample. The detection of such antibodies provides information concerning not only exposure to particular antigens, but can also provide information concerning progression of disease. Antibody capture assays that utilize solid-phase antigens, however, do not allow the measurement of real antibody titers in a sample. Assays for the detection and/or quantitation of at least two different substances in a test sample have been described. U.S. Pat. No. 5,395,752 (the '752 patent), incorporated herein by reference, describes chemiluminescent compounds as detectable markers for use in the detection of at least two substances in a test sample. Chemiluminescent compounds which emit light at different wavelengths with minimal overlap are utilized. The detectable markers, i.e., chemiluminescent compounds, however, are specific for the particular substance to be detected/quantitated in the test sample.

A method for assaying antibodies in a test sample that facilitates measurement of real titers, can accommodate the detections different antibody species directed against the same source in a test sample, as well as accommodate the detection of different antibodies against different sources in a test sample is needed.

SUMMARY OF THE INVENTION

In one aspect, the present invention relates to a method for the detection/quantitation of antibodies to a particular target antigen in a sample in a single incubation step.

In another aspect, the present invention relates to a method for the detection/quantitation of antibodies to at least two antigens from the same source in a single test sample in a single incubation step, using a single detectable marker.

In yet another aspect, the present invention relates to a method for the detection/quantitation of antibodies to at least two antigens from the same source in a single test sample in a single incubation step, using at least two light reagents which emit light at different wavelengths as the detectable markers.

In a further aspect, the present invention relates to a method for the detection of antigens from more than one source in a single test sample, in a single incubation step, using light reagents which emit light at different wavelengths as the detectable markers. In a further aspect, the present invention relates to a method for the determination of an antibody profile and real antibody titer for a particular source in test samples from a single subject using a single detectable marker.

In a further aspect, the present invention relates to test kits comprising compartments for performing the methods according to the invention. In the kits according to the invention, the solid phase and detectable marker can be stored in the same compartment.

DETAILED DESCRIPTION

Figure 1:
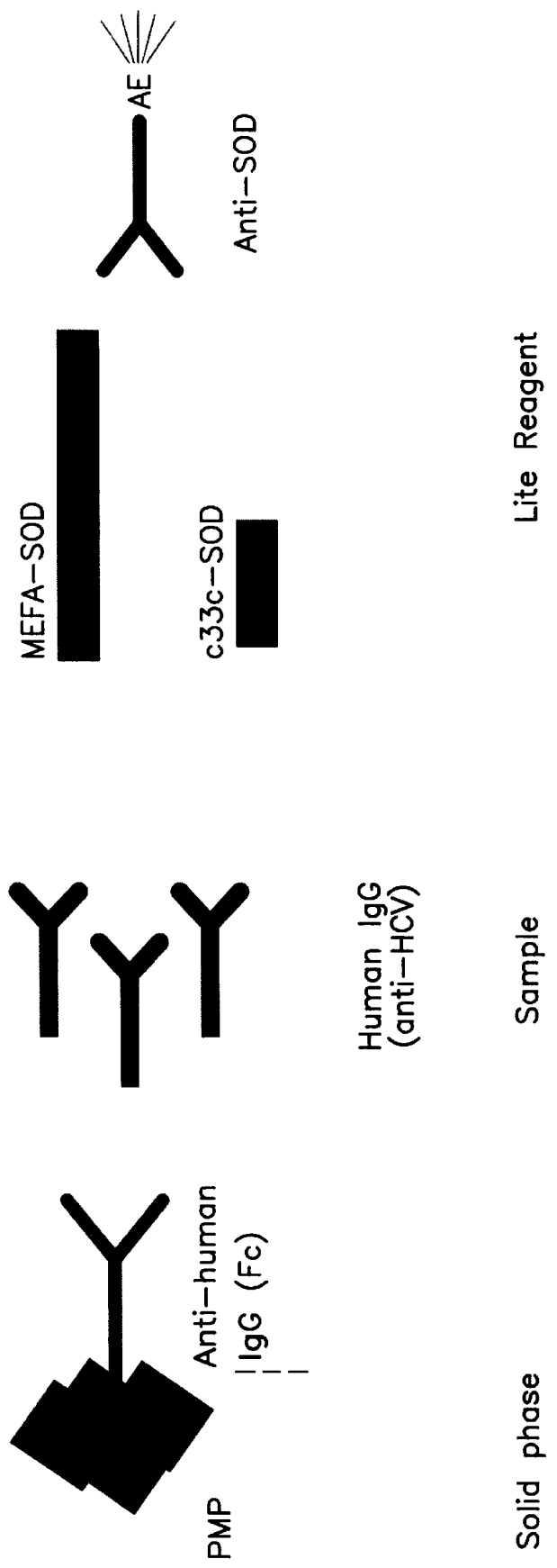
FIG. 1 depicts an exemplary assay format according to the invention.

The practice of the present invention will employ, unless otherwise indicated, conventional methods of virology, immunology, microbiology, molecular biology and recombinant DNA techniques within the skill of the art. Such techniques are explained fully in the literature. See, e.g., Sambrook, et al., *Molecular Cloning: A Laboratory Manual* (2nd Edition, 1989); *DNA Cloning: A Practical Approach*, Vols. I & II (D. Glover, ed.); *Methods In Enzymology* (S. Colowick and N. Kaplan eds., Academic Press, Inc.); *Handbook of Experimental Immunology*, Vols. I–IV (D. M. Weir and C. C. Blackwell eds., Blackwell Scientific Publications); and *Fundamental Virology*, 2nd Edition, Vols. I & II (B. N. Fields and D. M. Knipe, eds.).

Assays for the detection of antibodies against a single target antigen, multiple target antigens from the same source, or multiple target antigens from different sources in a single test sample, that can be performed in a single incubation step (i.e., simultaneously) are described. The assays can be performed on a high throughput, automated system and, thus, allow for data renormalization. The assays according to the invention exhibit high sensitivity (100%) and specificity (99.5–99.7% on blood donor samples). Universal solid phases and/or universal detectable markers are employed.

The following definitions are employed herein.

The term "target antigen" as used herein includes single epitope and multiple epitope antigens, as well as haptens.

The term "source" as used in reference to the target antigens herein includes, without limitation, viruses, bacteria, tumors, fungi, etc. The different sources can be, for example, different subtypes of a virus, different viruses, or a virus and a bacteria.

The term "ligand" as used herein refers to a binding partner. In preferred embodiments, the ligands are superoxide dismutase ("SOD") and ubiquitin.

The term "detectable marker" as used herein includes, but is not limited to, a chromophore, an enzyme, an enzyme reactive compound whose cleavage product is detectable, rhodamine, biotin, streptavidin, a fluorescent compound, a chemiluminescent compound, and derivatives and/or combinations of these markers. In the examples provided, the chemiluminescent compound dimethyl acridinium ester (DMAE, Ciba Corning Diagnostics Corp.) was used. Labeling with any marker is carried out under conditions for obtaining optimal detection and binding of the antibody.

The means for detecting the detectable markers will depend upon the marker used. The appropriate means, and conditions, can be readily determined by one of ordinary skill in the art. As set forth in the examples below, when DMAE is the detectable marker in an assay, the resultant anti-ligand-DMAE conjugate is the tracer, with DMAE detectable by light emission when reacted with NaOH/$H_2O_2$. In the assays involving two or more light reagents, at least two photomultiplier tubes must be utilized to obtain the measurements.

The labeling of individual antigens with detectable markers can be very tedious and, further, the resultant label may not be stable. The present invention provides for a universal detectable marker. In the present invention, the antigens are coupled to a ligand, e.g., an antigen/ligand fusion protein.

This fusion protein is paired with a detectable marker comprising an antibody directed against the ligand. The antibody directed against the ligand is coupled to the detectable marker. Many different antigens can be fused to the same ligand. In this manner, numerous antigens can be detected with a single, universal marker.

The term "subject" as used herein refers to the source of the test sample, and includes, without limitation, humans and other vertebrates. In a preferred embodiment, the subject is human. The term "test sample" as used herein refers to any biological fluid from a subject in which antibodies against the target antigens may be present including, but not limited to, serum and plasma.

"Anti-subject immunoglobulin antibodies" refers to antibodies directed against immunoglobulins from the subject in general. In a preferred embodiment, the anti-subject immunoglobulin antibodies are rat anti-human immunoglobulin (Ig). In a more preferred embodiment, the anti-subject human antibodies are rat anti-human IgG. The anti-subject immunoglobulin antibodies are coupled to the solid phase providing, thus, a universal solid phase for detecting/quantitating antibody in a test sample.

The solid phase can be paramagnetic microparticles ("PMP"), magnetic latex particles ("MLP"), or microtiter plates. Preferably, the particles are less than approximately 10 μm in diameter.

The test kits according to the invention also include calibrators or controls. As noted above, in preferred embodiments, the target antigens are coupled to the ligands as fusion proteins. For example, the antigens can be expressed as internal antigens within the yeast *S. cerevisiae* as C-terminal fusions with human SOD using methods described previously for the generation of the c100-3 (NS4, 363 aa) Hepatitis C virus antigen. Kuo et al., *Science*, 1989, 244, 362–364, incorporated herein by reference in its entirety; and Cousens et al., *Gene*, 1987, 61, 265–275, incorporated herein by reference in its entirety. The c33c antigen (NS3, 363 amino acids) has also been expressed as an internal SOD fusion polypeptide in *E. coli* by methods described for the synthesis of 5-1-1 antigen. Choo et al., *Science*, 1989, 244, 359–362, incorporated herein by reference in its entirety. The recombinant HCV antigens were purified as described in Chien et al., *Proc. Natl. Acad. Sci. USA*, 1989, 89, 10011–10015. In the specific examples detailed below, all antigens were prepared as SOD fusion proteins. However, other suitable fusion proteins can be made depending upon the availability of appropriate antibodies that recognize the fusion partner ligand.

MEFA-6 is a multiple epitope antigen and contains epitopes from the core, envelope, NS3, NS4 and NS5 regions of the hepatitis C polyprotein, including equivalent antigenic determinants from HCV strains 1, 2, and 3. The various DNA segments coding for the HCV epitopes were constructed by PCR amplification or by synthetic oligonucleotides. MEFA-6 antigen includes multiple copies of HCV epitopes from the core and NS5 region; different serotype epitopes from the NS4 5-1-1 region; a single copy of major linear epitopes from the c100 C-terminal regions, E1, and E2 regions, as well as the HCV NS3 (c33c) region. The general structural formula for the MEFA-6 fusion protein is hSOD-E1-E2-c33c-5-1-1(type 1)-5-1-1(type 3)-5-1-1(type 2)-c100-NS5(2 copies)-core(2 copies). This antigen has a very high expression level in yeast, purifies to a high degree of homogeneity, and exhibits high sensitivity and high selectivity in the immunoassays described below. MEFA-6 was prepared as described in application PCT US97/08950 filed May 23, 1997, incorporated herein by reference in its entirety.

Anti-SOD-DMAE was used as the universal detectable marker. The anti-SOD antibody was labeled with DMAE by reaction of amino acid side chains (e.g. lysine ε side chain or cysteine thiol) with a reactive moiety covalently linked to DMAE (see WO 95/27702, published Oct. 19, 1995, Ciba Corning Diagnostics Corp., herein incorporated by reference in its entirety). Thiols of amino acid side chains can be labeled using DMAE-ED-MCC or NSP-DMAE-PEG-BrAc (Ciba Corning). Labeling procedures were generally as described in WO 95/27702, incorporated herein by reference, with variations in conditions as necessary for each antigen to provide optimal detection and antigenicity.

Sensitivity was reported as the optical density of the assay sample divided by the assay detection cut off in optical density units (s/co). All known negative samples exhibited s/co values less than 1.

EXAMPLES

EXAMPLE 1

Manual Assay

A Magic Lite Analyzer System II (MLA II is used for the manual assay. Parameters such as volume, concentration, time, and temperature are provided for guidance, but may be adjusted accordingly. Briefly, a 10 μl aliquot of test sample was added to five separate 75×12 mm test tubes for obtaining an antibody profile for HCV. To each tube, 100 μl of sample diluent or buffer, 100 μl of solid phase buffer containing paramagnetic particles (PMP) conjugated to rat anti-human IgG antibodies (PMP/anti-human IgG, 30 μg/assay), 50 μl HCV antigen/SOD fusion proteins (core (c22-3, 50 ng), NS3 (c33c, 100 ng), NS4 (c-100-3 100 ng), NS4 (5-1-1 100 ng), and NS5 (100 ng), and 100 μl anti-SOD conjugated to DMAE (30 million relative light units, "RLU") in ligand reagent (LR) diluent were added, and incubated for 18 minutes at 37° C. The solid phase/Lite reagent diluent buffer comprised 50 mM Tris, 0.5 M KCl, 1 mM disodium EDTA, 3.75% BSA, 0.003% Yeast, 0.05 g/L *E. coli* extract, 0.5% Tween-20, 2 mg/L Amphotericin B, 24 mg/L Gentamicin Sulfate, 30 μg/test Solid Phase and 45×10$^6$ test Lite Reagent (anti-SOD*DMAE antibodies). The ancillary diluent buffer comprised 50 mM Tris, 0.5M KCl, 1 mM disodium EDTA, 3.75% BSA, 0.003% Yeast, 0.05 g/L *E. coli*, 0.5% Tween-20, 2 mg/L Amphotericin B, 24 mg/L Gentamicin Sulfate, 0.05 g/L Ascites IgG1 and 0.1 g/L Ascites IgG2A (blocking antibodies). The wash reagent comprised PBS/Tween-20. The acid reagent comprises 0.5% $H_2O_2$/0.1 N $HNO_3$. The base reagent comprises <0.25N NaOH with surfactant.

The sample tubes were placed on a magnet for sufficient time to sediment the PMP particles. The samples were decanted using a magnet to retain the PMP particles. The PMP particles were washed twice with vortexing in 1 mL of PBS. The wash solution was PBS, 0.1% Tween-20, 0.09% $NaN_3$, and 1 mM EDTA. The steps of mixing, incubating, sedimenting and decanting may be repeated at least one time. To each tube 100 μl of water was added to resuspend the PMP particles. The tubes were then placed in an MLA-II instrument and light emission measured for 2 seconds.

Results, using chronic paid donor samples, are presented in Table 1.

EXAMPLE 2

Comparison of Automated Assay with Other Commercial Assays

The manual anti-HCV assay described above was adapted for automated use using an ACS:Centaur apparatus. The following procedure is used. Briefly, the ACS:Centaur system automatically performs the following steps: 1) dispenses 10 μl of sample into a cuvette; 2) dispenses 100 μl of ancillary diluent buffer, 100 μl of Lite Reagent/Solid Phase, 50 μl of antigen reagent 2 (e.g., MEFA-6), 50 μl of antigen reagent 1 (e.g., c33c) and incubates the mixture for 18 minutes at 37° C.; 3) separates the solid phase from the mixture and aspirates the unbound reagent; 4) washes the cuvette with wash reagent 1; 5) dispenses 300 μl each of acid reagent and base reagent to initiate the chemiluminescent reaction; and 6) reports results according to the selected option, as described in the system operating instructions or in the online help system.

The solid phase/Lite reagent diluent buffer comprised 50 mM Tris, 0.5 M KCl, 1 mM disodium EDTA, 3.75% BSA, 0.003% Yeast, 0.05 g/L E. coli extract, 0.5% Tween-20, 2 mg/L Amphotericin B, 24 mg/L Gentamicin Sulfate, 30 μg/test Solid Phase and 45×10$^6$ test Lite Reagent (anti-SOD*DMAE antibodies). The ancillary diluent buffer comprised 50 mM Tris, 0.5M KCl, 1 mM disodium EDTA, 3.75% BSA, 0.003% Yeast, 0.05 g/L E. coli, 0.5% Tween-20, 2 mg/L Amphotericin B, 24 mg/L Gentamicin Sulfate, 0.05 g/L Ascites IgG1 and 0.1 g/L Ascites IgG2A (blocking antibodies). The wash reagent comprised PBS/Tween-20. The acid reagent comprises 0.5% $H_2O_2$/0.1 N $HNO_3$. The base reagent comprises <0.25N NaOH with surfactant.

Results were compared to the Ortho 3.0, Abbott 3.0, and RIBA® 3.0 assays using commercially available seroconversion panels and are depicted in Table II. Results for the Ortho, Abbott, and RIBA® assays are provided by the vendors for the seroconversion panels: BBI (BBI) refers to Boston Biomedica Incorporated and BCP refers to BioClinical Partners. PHV is a prefix to designate the panel name. Lots #1 through #4 refer to multiple lots of reagents from dits (reagent compartment plus solid phase).

As is evident from the results, the assay according to the present invention allowed the detection of antibody several bleeds earlier than Ortho 3.0 and Abbott 3.0. The RIBA® assay confirms HCV invention.

EXAMPLE 3

Sensitivity of Automated Assay

The sensitivity of the assay according to the present invention was ascertained in a test population of 510 patients that screened positive in the Ortho 3.0 assay. Assay conditions were as described above. The results of the testing are depicted in Table III. In the Table, "IVDA" refers to IV drug abuse, "STD" refers to sexually transmitted disease, "N" refers to the number of samples in each group tested, and "RR" refers Repeat Reactive. Samples that are initially reactive (positive) in the assay are retested; if the sample is reactive (positive) upon repeat testing it is considered "Repeat Reactive."

As is seen from Table III, all samples which tested positive for HCV in the RIBA® 3.0 assay were Repeat Reactive using the assay according to the present invention.

EXAMPLE 4

Assay for Multiple Viruses in a Single Sample

Assay conditions are as described in Example 3 above with the exception that a different ligand and different light reagent are used for each antigen. MEFA-6-SOD is used and detected with anti-SOD-DMAE; c33c-ubiquitin is used and detected with anti-ubiquitin-LEAE (long wavelength emitting acridinium ester).

The foregoing examples are meant to illustrate the invention and are not to be construed to limit the invention in any way. Those skilled in the art will recognize modifications that are within the spirit and scope of the invention. All references cited herein are hereby incorporated by reference in their entirety.

TABLE I

HCV Multi-Antigen assay: anti-SOD*DMAE format on the MLA II

| | | HCV recombinant SOD Fusion antigens | | | | |
|---|---|---|---|---|---|---|
| | | 50 ng/assay Core (c22-3) s | 100 ng/assay NS-3 (c33c) s | 100 ng/assay NS-4 (c-100-3) s | 100 ng/assay NS-4 (5-1-1) s | 100 ng/assay NS-5 s |
| HCV | LL57386 | 111604 | nd | 2156 | 1709 | nd |
| Chronic | 96727 | 54993 | 385524 | 6822 | 2880 | 74921 |
| paid donor | FF2594 | 32848 | 254803 | 49829 | 162193 | 2680 |
| samples | FF2589 | 509909 | nd | 7330 | 20174 | nd |
| | FF2567 | 20913 | nd | 5158 | 2094 | nd |
| random | r1 | 8100 | 1001 | 2079 | 1032 | 2526 |
| negatives | r2 | 7839 | 1232 | 1956 | 955 | 2649 |
| | r3 | 5606 | 1032 | 1833 | 1201 | 3018 |
| | r4 | 7099 | 1170 | 1432 | 1155 | 2402 |
| | | s/co | s/co | s/co | s/co | s/co |
| | LL57366 | 5.2 | nd | 0.4 | 0.5 | nd |
| | 96727 | 2.6 | 115.9 | 1.2 | 0.9 | 9.4 |
| | FF2594 | 1.5 | 79.6 | 10.9 | 40.8 | 0.3 |
| | FF2589 | 23.7 | nd | 1.3 | 6.2 | nd |
| | FF2567 | 1.0 | nd | 0.9 | 0.6 | nd | cutoff equal or greater than 1.0 is positive

TABLE II

Seroconversion Sensitivity of ACS:Centaur HCV Assay
(Earlier Detection)

| | Day | Lot #1 Index | Lot #2 Index | Lot #3 Index | Lot #4 Index | Ortho 3.0 S/CO | Abbott 3.0 S/CO | RIBA 3.0 | | | | |
|---|---|---|---|---|---|---|---|---|---|---|---|---|
| | | | | | | | | c100 | c33 | c22 | NS5 | 80D |
| BB1 | | | | | | | | | | | | |
| PHV905-02 | 4 | 0.2 | 0.5 | 0.3 | 0.3 | 0.0 | 0.1 | – | – | – | – | – NEG |
| PHV905-03 | 7 | 0.4 | 0.5 | 0.5 | 0.4 | 0.0 | 0.1 | – | – | – | – | – NEG |
| PHV905-04 | 11 | 1.3 | 1.3 | 1.4 | 1.4 | 0.2 | 0.1 | – | 1+ | – | – | – IND |
| PHV905-05 | 14 | 1.6 | 1.7 | 1.7 | 1.6 | 0.6 | 0.2 | – | 1+ | – | – | – IND |
| PHV905-06 | 18 | 3.2 | 2.9 | 2.9 | 3.0 | 1.0 | 0.3 | – | 1+ | +/– | – | – IND |
| PHV905-07 | 21 | 6.7 | 5.8 | 5.7 | 5.6 | 2.3 | 0.6 | – | 2+ | 1+ | – | – POS |
| PHV905-08 | 25 | 16.0 | 15.5 | 16.4 | 13.5 | 4.6 | 3.4 | – | 4+ | 4+ | – | – POS |
| PHV905-09 | 28 | 38.6 | 34.1 | 38.3 | 32.6 | >4.9 | >4.9 | – | 4+ | 4+ | – | – POS |
| BB1 | | | | | | | | | | | | |
| PHV907-03 | 7 | | | 0.3 | 0.3 | 0.0 | 0.1 | – | – | – | – | – NEG |
| PHV907-04 | 13 | | | 0.5 | 0.4 | 0.1 | 0.2 | – | – | 1+ | – | – IND |
| PHV907-05 | 18 | | | 1.8 | 1.4 | 0.5 | 0.8 | – | +/– | 4+ | – | – IND |
| PHV907-06 | 21 | | | 3.9 | 3.2 | 1.0 | 1.4 | – | 1+ | 4+ | – | – POS |
| PHV907-07 | 164 | | | | | >5.0 | >5.0 | | | | | |
| BCP 6214 (61083) | | | | | | | | | | | | |
| 6214-06 | 8 | 0.3 | 0.3 | | | 0.0 | | – | – | – | – | – NEG |
| 6214-07 | 23 | 0.3 | 0.4 | | | 0.0 | | – | +/– | – | – | – NEG |
| 6214-08 | 25 | 0.5 | 0.5 | | | 0.0 | | +/– | +/– | – | – | – NEG |
| 6214-09 | 30 | 2.0 | 2.1 | | | 0.9 | | +/– | 2+ | – | – | – IND |
| 6214-10 | 32 | 3.3 | 3.2 | | | 2.6 | | +/– | 3+ | – | – | – IND |
| 6214-11 | 49 | 28.1 | 25.4 | | | 4.1 | | 2+ | 4+ | – | – | – POS |

TABLE III

Sensitivity of ACS:Centaur HCV 4.0 Assay Using
Populations (n = 510) Screened Positive with Ortho HCV 3.0

| | N | RR | Confirmed | Sensitivity |
|---|---|---|---|---|
| Hemophiliac | 10[a] | 9 | 9 | 100% |
| IVDA | 32[b] | 31 | 31 | 100% |
| Dialysis | 20 | 20 | 20 | 100% |
| STD | 56[c] | 54 | 54 | 100% |
| Hospital | 65[d] | 58 | 58 | 100% |
| Egyptian, Chinese Brazilian, Japanese | 138[e] | 137 | 137 | 100% |
| Verified HCV Serology | 189 | 189 | 189 | 100% |

[a]One sample was RIBA 3.0 negative
[b,e]One sample was RIBA 3.0 indeterminate (c33c)
[c]One was RIBA 3.0 indeterminate (NS5), 1 was RIBA 3.0 negative
[d]5 were RIBA 3.0 indeterminate (3-c22, 1-NS5, 1-c33), 2 were RIBA 3.0 negative

We claim:

1. A method for detecting/quantitating antibodies to a target antigen in a test sample from a subject, said method comprising:
   a) simultaneously incubating said test sample with
      i) solid phase anti-subject immunoglobulin antibodies,
      ii) a fusion protein comprising the target antigen coupled to a ligand, and
      iii) an anti-ligand antibody coupled to a detectable marker to effect a reaction between:
         anti-target antigen antibodies in the test sample from the subject, the solid phase anti-subject immunoglobulin antibodies, the target antigen coupled to a ligand, and the anti-ligand antibody coupled to a detectable marker; and
   b) detecting the detectable marker by appropriate means.

2. The method of claim 1 wherein said target antigen is at least one epitope of Hepatitis C virus.

3. The method of claim 2 wherein said target antigen contains at least two epitopes of Hepatitis C virus.

4. The method of claim 2 wherein said target antigen is an NS3 antigen from Hepatitis C virus.

5. The method of claim 3 or 4 wherein said ligand is superoxide dismutase (SOD).

6. The method of claim 3 or 4 wherein said detectable marker is a chemiluminescent reagent.

7. The method of claim 6 wherein said chemiluminescent reagent is an acridinium ester.

8. A method for detecting/quantitating antibodies to two or more target antigens in a test sample from a subject, wherein said target antigens are from the same source, said method comprising:
   a) simultaneously incubating said test sample with
      i) solid phase anti-subject immunoglobulin antibodies,
      ii) a fusion protein comprising a first target antigen coupled to a ligand,
      iii) at least a second target antigen coupled to said ligand, and
      iv) anti-ligand antibodies coupled to a detectable marker to effect a reaction between:

anti-first target antigen antibodies in the test sample from the subject, said solid phase anti-subject immunoglobulin antibodies, the first target antigen coupled to a ligand, and the anti-ligand antibody coupled to a detectable marker; and between:

anti-second target antigen antibodies in the test sample from the subject, said solid phase anti-subject immunoglobulin antibodies, the at least second target antigen coupled to said ligand, and the anti-ligand antibody coupled to a detectable marker; and b) detecting the detectable marker by appropriate means.

9. The method of claim 8 wherein said source is Hepatitis C virus.

10. The method of claim 8 wherein said first target antigen is an NS3 antigen from Hepatitis C virus.

11. The method of claim 8 wherein said at least a second target antigen is a core antigen from Hepatitis C virus.

12. The method of claim 10 or 11 wherein said ligand is SOD.

13. The method of claim 10 or 11 wherein said detectable marker is a chemiluminescent reagent.

14. The method of claim 13 wherein said chemiluminescent reagent is an acridinium ester.

15. A method for detecting/quantitating antibodies to two or more target antigens in a test sample from a subject, wherein said target antigens are from different sources, said method comprising:

a) simultaneously incubating said test sample with
  i) solid phase anti-subject immunoglobulin antibodies,
  ii) a fusion protein comprising a first target antigen coupled to a first ligand,
  iii) at least a second target antigen coupled to a second ligand,
  iv) anti-first ligand antibodies coupled to a first light reagent, and
  v) at least an anti-second ligand antibody coupled to a second light reagent to effect a reaction between:

anti-first target antigen antibodies in the test sample from the subject, said solid phase anti-subject immunoglobulin antibodies, the first target antigen coupled to a first ligand, and the anti-first ligand antibody coupled to a first light reagent; and between:

anti-second target antigen antibodies in the test sample from the subject, said solid phase anti-subject immunoglobulin antibodies, the at least second target antigen coupled to a second ligand, and the anti-second ligand antibody coupled to a second light reagent, wherein said first and at least said second light reagents emit light of detectably different wavelengths; and b) detecting the emission signal of each of said light reagents.

16. The method of claim 15 wherein said different sources are subtypes of the same virus.

17. The method of claim 15 wherein said different sources are different viruses.

18. The method of claim 15 wherein said first ligand is SOD.

19. The method of claim 15 wherein said second ligand is ubiquitin.

20. The method of claim 15 wherein at least one of said light reagents is an acridinium ester.

21. The method of claim 15 wherein said first and second target antigens coupled to said first and second ligands are fusion proteins.

22. A test kit for the detection of antibodies directed to one or more target antigens in a test sample in a single incubation step, wherein said target antigens are from the same source, said test kit comprising compartments, solid phase anti-subject immunoglobulin antibodies, a fusion protein comprising at least a first target antigen coupled to a first ligand, and an anti-first ligand antibody coupled to a detectable marker.

23. The test kit of claim 22 wherein said ligand is SOD.

24. The test kit of claim 22 wherein said detectable marker is a chemiluminescent reagent.

25. The test kit of claim 24 wherein said detectable marker is an acridinium ester.

26. The test kit of claim 24 wherein the solid phase anti-subject immunoglobulin antibodies and detectable marker are stored in the same compartment.

27. The test kit of claim 22 further comprising a second target antigen coupled to said first ligand.

28. A test kit for the detection of antibodies directed to two or more target antigens in a test sample in a single incubation step, wherein said target antigens are from different sources, said test kit comprising compartments, solid phase anti-subject immunoglobulin antibodies, a fusion protein comprising a first target antigen coupled to a first ligand, at least a second target antigen coupled to a second ligand, an anti-first ligand antibody coupled to a first light reagent, and at least an anti-second ligand antibody coupled to a second light reagent, wherein said first and at least said second light reagents emit light emission signals of detectably different wavelengths.

29. The test kit of claim 28 wherein said detectable marker is a chemiluminescent reagent.

30. The test kit of claim 28 wherein said detectable marker is an acridinium ester.

31. The test kit of claim 28 wherein said first ligand is SOD.

32. The test kit of claim 28 wherein said second ligand is ubiquitin.

33. The test of claim 28 wherein the solid phase anti-subject immunoglobulin antibodies and detectable marker are stored in the same compartment.

* * * * *